(12) United States Patent
Haider et al.

(10) Patent No.: US 9,402,974 B2
(45) Date of Patent: Aug. 2, 2016

(54) OPTIMIZED INTRACRANIAL CATHETERS FOR CONVECTION-ENHANCED DELIVERY OF THERAPEUTICS

(75) Inventors: M. Ishaq Haider, Cary, NC (US); Frank Martin, Durham, NC (US); Bruce Clyde Roberts, Hillsborough, NC (US); Jason B. Alarcon, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 402 days.

(21) Appl. No.: 13/143,536

(22) PCT Filed: Jan. 11, 2010

(86) PCT No.: PCT/US2010/020616
§ 371 (c)(1),
(2), (4) Date: Sep. 6, 2011

(87) PCT Pub. No.: WO2010/081072
PCT Pub. Date: Jul. 15, 2010

(65) Prior Publication Data
US 2012/0041394 A1  Feb. 16, 2012

Related U.S. Application Data

(60) Provisional application No. 61/144,027, filed on Jan. 12, 2009.

(51) Int. Cl.
*A61M 25/00* (2006.01)
*A61M 25/06* (2006.01)

(52) U.S. Cl.
CPC ......... *A61M 25/0068* (2013.01); *A61M 25/007* (2013.01); *A61M 25/0606* (2013.01)

(58) Field of Classification Search
CPC ............. A61M 2025/0031; A61M 25/0029; A61M 2025/0034; A61M 25/0032; A61M 25/0082; A61M 2039/0211; A61M 2205/32; A61M 25/0068; A61M 25/007; A61M 25/0606; A61B 17/34; A61B 17/3415
USPC ........... 604/164.01, 164.09–165.02, 272, 264
See application file for complete search history.

(56) References Cited

U.S. PATENT DOCUMENTS

| | | | | |
|---|---|---|---|---|
| 3,720,210 A * | 3/1973 | Diettrich | ............... | A61B 17/34 604/164.01 |
| 4,180,068 A * | 12/1979 | Jacobsen | ............... | A61B 17/34 604/164.01 |
| 4,531,937 A * | 7/1985 | Yates | ............... | A61M 25/0097 604/122 |
| 5,279,551 A * | 1/1994 | James | ............... | A61B 17/3421 604/164.01 |

(Continued)

FOREIGN PATENT DOCUMENTS

WO    2008/091652 A2    7/2008

*Primary Examiner* — Emily Schmidt
*Assistant Examiner* — Lauren M Peng
(74) *Attorney, Agent, or Firm* — J. Timothy Meigs; Craig Metcalf; Kirton McConkie

(57) ABSTRACT

A primable catheter including a thermoreactive, viscoelastic material that is internally supported with a trocar wire. The primable catheter further includes a multi-chamfered tip and a gap interposed between an inner surface of the catheter and the outer surface of the trocar, such that a priming fluid is permitted to flow through the catheter and purge air trapped between the trocar and the inner surface of the catheter. Following insertion of the catheter, the trocar is removed and a therapeutic is infused via the catheter.

21 Claims, 7 Drawing Sheets

(56) References Cited

U.S. PATENT DOCUMENTS

| | | |
|---|---|---|
| 5,527,276 A | 6/1996 | Bruce |
| 5,720,720 A | 2/1998 | Laske et al. |
| 5,968,022 A * | 10/1999 | Saito ............... B24B 19/16 604/264 |
| 6,024,725 A * | 2/2000 | Bollinger ............ A61M 39/06 604/164.01 |
| 6,595,966 B2 * | 7/2003 | Davey et al. ............ 604/264 |
| 7,381,200 B2 * | 6/2008 | Katoh ............... A61M 25/0084 604/164.01 |
| 7,566,316 B2 * | 7/2009 | McGuckin, Jr. ...... A61M 1/285 604/164.13 |
| 7,963,956 B2 | 6/2011 | Kunst |
| 7,972,305 B2 | 7/2011 | Mittermeyer |
| 2005/0075625 A1 * | 4/2005 | Dao ............... A61B 17/12022 604/523 |
| 2006/0020247 A1 * | 1/2006 | Kagan ............. A61B 17/00234 604/264 |
| 2006/0270962 A1 * | 11/2006 | McGuckin, Jr. ...... A61M 1/285 604/6.16 |
| 2010/0145265 A1 * | 6/2010 | Min ............... A61M 25/0068 604/95.03 |

* cited by examiner

OPTIMIZED INTRACRANIAL CATHETERS FOR CONVECTION-ENHANCED DELIVERY OF THERAPEUTICS

This application is a National Stage of International Application No. PCT/US2010/020616, filed Jan. 11, 2010, and entitled OPTIMIZED INTRACRANIAL CATHETERS FOR CONVECTION-ENHANCED DELIVERY OF THERAPEUTICS which claims the benefit of U.S. Provisional Application No. 61/144,027, filed Jan. 12, 2009. This application claims priority to and incorporates herein by reference the above-referenced applications in their entirety.

BACKGROUND OF THE INVENTION

The present invention relates to a primable catheter system for use in any targeted drug delivery procedure including convection-enhanced delivery (CED) and chronic intracranial administrations. CED is the continuous injection under positive pressure of a fluid containing a therapeutic agent. This technique is especially useful for administering therapeutic agents to tissues that inaccessible via traditional oral medications or venous infusion techniques. For example, for central nervous system (CNS) applications, drug delivery by systemic or by intrathecal methods is not very effective because of the blood-brain barrier and limitations with regard to the drug diffusion into the tissue. At best, traditional methods of treatment result in incomplete, non-targeted and heterogeneous dispersion throughout the CNS.

CED may be used to overcome some of the restrictions associated with traditional and other delivery systems. CED utilizes a pressure gradient to infuse substances directly into the interstitial space of a target tissue, for example a solid tumor tissue, via a catheter. This process is known as interstitial infusion and relies on bulk, convective flow and can be used to distribute both small and large molecular weight substances over clinically relevant volumes within solid tissue. Additional benefits include the ability to deliver the therapeutic at relatively constant concentrations throughout the volume of distribution.

Unfortunately, the present state of the technology for CED is unable to control fluid leakage into the brain interstitial space, and in particular control serious side effects caused by fluid leakage into the cerebrospinal fluid (CSF) and other vital regions. Fluid leakage commonly follows tissue damage incurred during insertion of the catheter into the target tissue. Due to the small gauge of the catheter, a rigid catheter guide is used with the catheter to guide the catheter into position. Upon insertion of the catheter, the catheter guide cuts through the target tissue resulting in trauma and tissue damage. As the fluid is injected through the catheter, the fluid leaks into the damaged tissue resulting in undesirable and serious side effects.

Another CED concern is air bubble formation and entrapment in the catheter line that causes therapeutic problems due to incomplete drug delivery to the intended target. As air within the catheter is injected into the target tissue, an air pocket is formed into which the therapeutic agent pools and distributes unevenly. Additionally, use of a catheter guide creates space between the target tissue and the outer surface of the catheter which results in retrograde flow of the therapeutic. Retrograde flow may result in underexposure of the intended target tissue with the therapeutic agent.

Thus, while methods currently exist for CED applications, challenges still exist. Accordingly, there is a need in the art for a primable catheter system that provides bulk delivery of therapeutics without the drawbacks of currently available methods. Such a primable catheter system is disclosed herein.

BRIEF SUMMARY OF THE INVENTION

The present invention relates to a primable catheter system for use in any targeted drug delivery procedure including convection-enhanced delivery (CED) and chronic intracranial administrations. Specifically, the present invention provides a catheter that includes an unobstructed lumen that is capable of being injected with a priming solution to purge air from within the lumen. In some embodiments the catheter is made of a metallic material, such as stainless steel or an alloy thereof. In other embodiments, the catheter is made of a thermoreactive viscoelastic polymer material that becomes more flexible when exposed to increased temperatures. For example, in some embodiments the catheter is made of a thermoreactive polymer that becomes more flexible when exposed to body temperature.

Viscoelastic catheters of the present invention generally lack sufficient rigidity to withstand forces associated with insertion into target tissues. In some embodiments, a supportive trocar is inserted through the lumen prior to insertion of the catheter. The trocar is made of a semi-rigid material, such as titanium or Nitinol and therefore possesses sufficient strength to guide the placement of the polymer catheter. The trocar further provides a cutting edge to initiate an opening in the target tissue. A tip portion of the catheter further includes multiple chamfered surfaces to smoothly reduce the diameter of the catheter to approximately the diameter of the trocar. As such, the catheter is gently introduced into the target tissue with minimal damage or trauma to the tissue.

Prior to insertion of the catheter, a priming fluid is injected into the catheter to purge air present within the catheter between the trocar and an inner surface of the catheter. In some embodiments a gap is positioned between the trocar and the inner surface of the catheter to provide a pathway through the interior of the catheter. This pathway permits the priming fluid and displaced air to exit the tip portion of the catheter thereby preparing the catheter for insertion into the target tissue. Following insertion of the catheter, the trocar is removed and a fluid is administered to the target tissue via the primed lumen. In some embodiments, the tip portion of the catheter further includes a plurality of side-ports or pores through which the infused liquid is dispersed in a diffusive manner.

Finally, in some embodiments the catheter includes multiple lumens each of which are separated by an interior wall. In some embodiments, the multi-lumen catheter includes a first lumen for housing a trocar, and a second lumen for administering a fluid to the target tissue. In other embodiments, the multi-lumen catheter further includes a third lumen for controlling and monitoring flow of a fluid to the target tissue.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
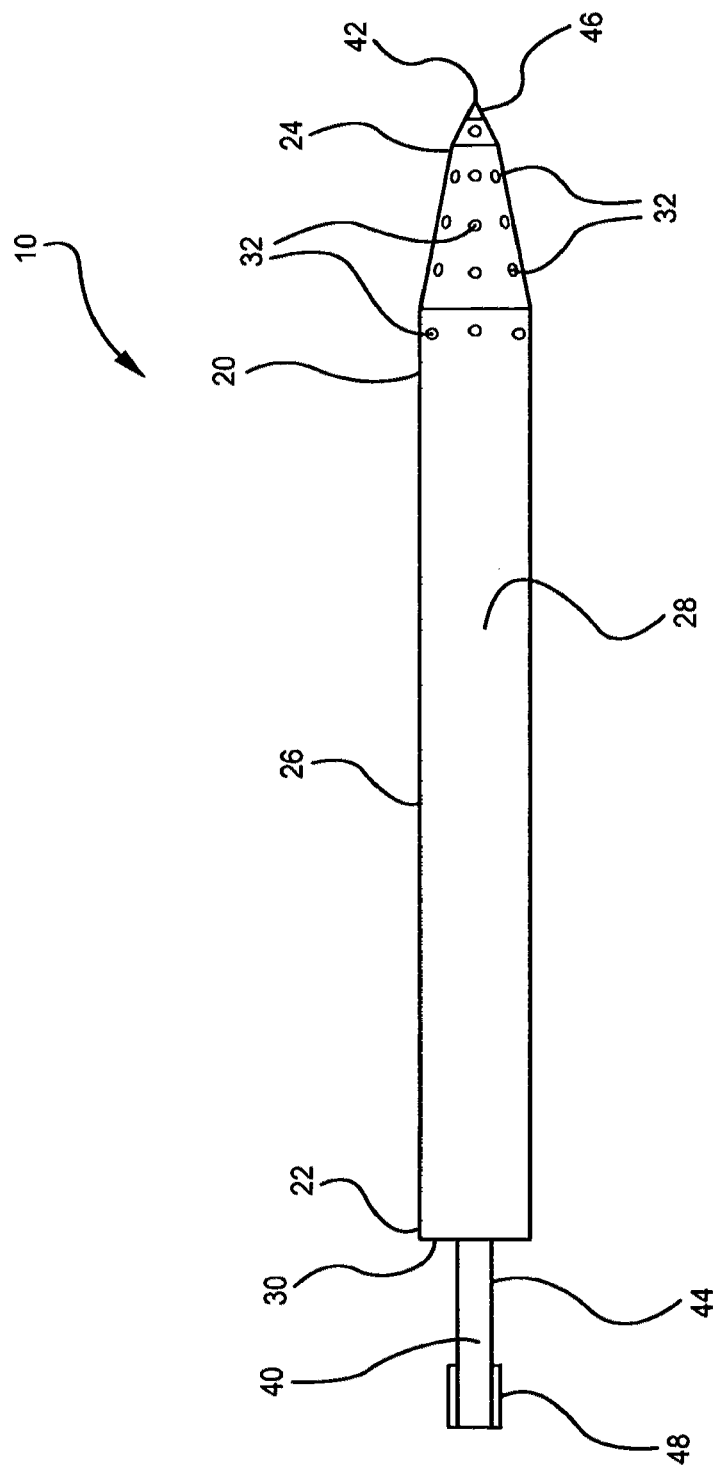
FIG. 1 is a perspective view of an implementation of a primable catheter system incorporating a supportive trocar.

Referring now to FIG. 1, a primable intracranial catheter delivery system 10 is shown. The primable catheter system 10 generally includes a catheter 20 having a base end 22, a tip end 24, and a middle portion 26. The catheter 20 also includes an outer surface 28 and an inner lumen 30 through which a stylet or trocar 40 may be inserted to provide rigidity to the system 10. In some embodiments of the catheter system 10, the catheter 20 comprises a rigid material, such as polyimide material or a non-ferrous MRI compatible metallic catheter having a sufficient gauge to enable insertion without the use of a trocar 40. In these embodiments, the gauge of the catheter 20 (30 gauge and larger diameters) and the design of the tip end 24 permit direct implantation into a target site without requiring additional structural elements, such as a trocar 40. In other embodiments, insertion of a smaller catheter 20 cannulae is desired thereby requiring the use of a trocar 40. For example, in some embodiments a 31 gauge, or smaller diameter, MRI compatible rigid material catheter 20 is installed in a target tissue, thereby requiring the use of a rigid trocar 40 to allow proper installation of the catheter 20. Following installation of the catheter 20, the trocar 40 is no longer needed and is therefore removed from the base end 22 of the catheter 20. Thus, the trocar 40 is useful for embodiments where the gauge or material of the catheter 20 is insufficient to permit unaided installation in a target tissue.

In some embodiments of the present invention, the catheter 20 is designed for insertion into sensitive tissues, such as central nervous system tissue including spinal cord and brain tissues. For these types of applications, a catheter 20 comprising a soft and flexible material is desired. Unlike a rigid catheter, a flexible catheter 20 material permits the brain or other sensitive tissue to move without incurring damage from the catheter. For example, in some embodiments the catheter 20 comprises a flexible or semi-flexible material, such as a thermoreactive, viscoelastic polymer. Thermoreactive, viscoelastic polymers include any suitable polymer material that becomes more elastic or flexible when exposed to increased temperatures. For example, a polyurethane-based material, such as Becton Dickinson's Nexira Vialon X-40, becomes soft and flexible when exposed to body temperature, yet maintains sufficient structural integrity and memory shape to accommodate proper fluid delivery. Although the polyurethane-based material lacks sufficient rigidity for unaided insertion, the tubing can be combined with a Nitinol trocar wire 40 to provide rigidity to the system 10 to help guide the tip 24 of the catheter 20 into the desired insertion location.

Figure 2:
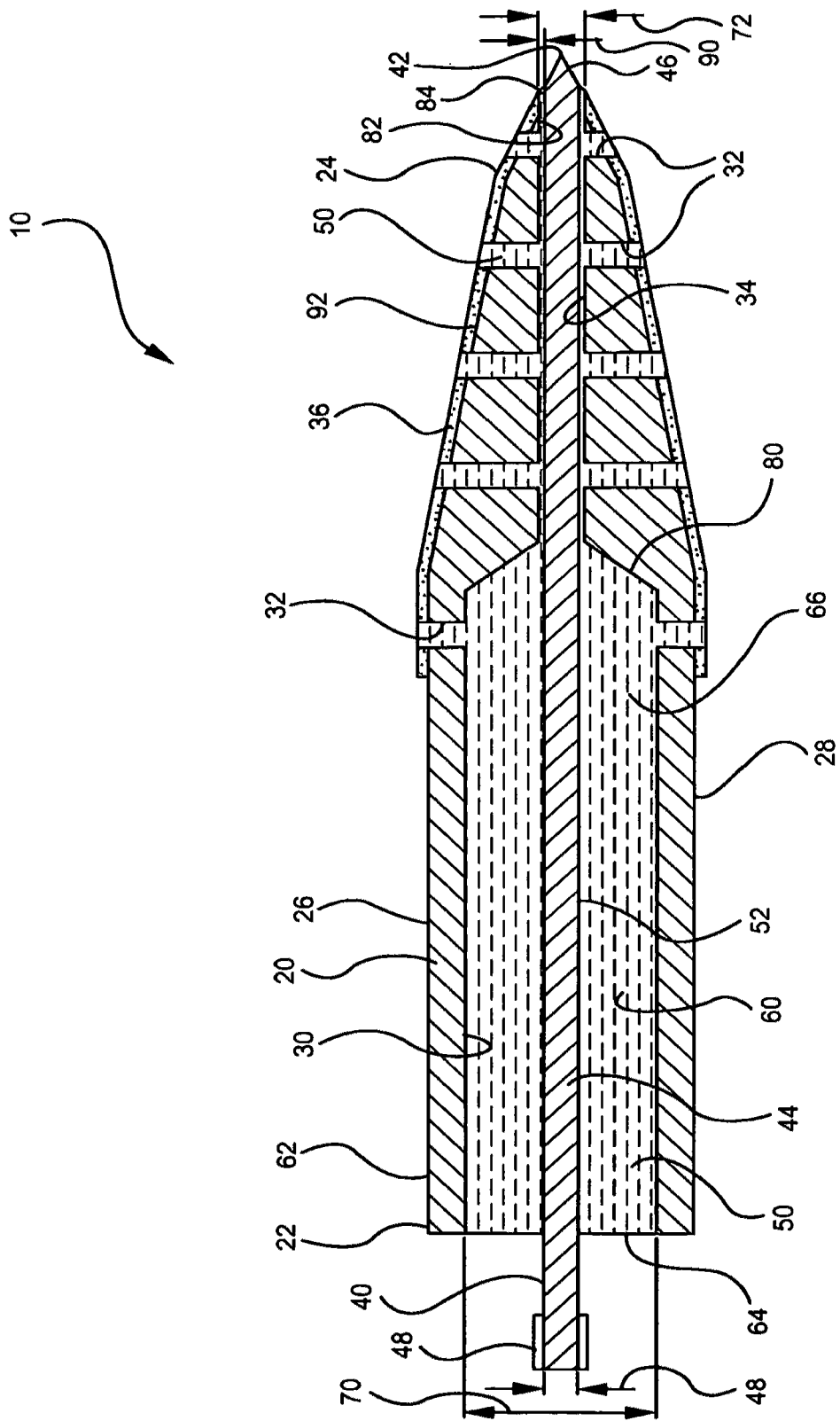
FIG. 2 is a cross-sectioned view of an implementation of a primable catheter system incorporating a supportive trocar.
Figure 4:
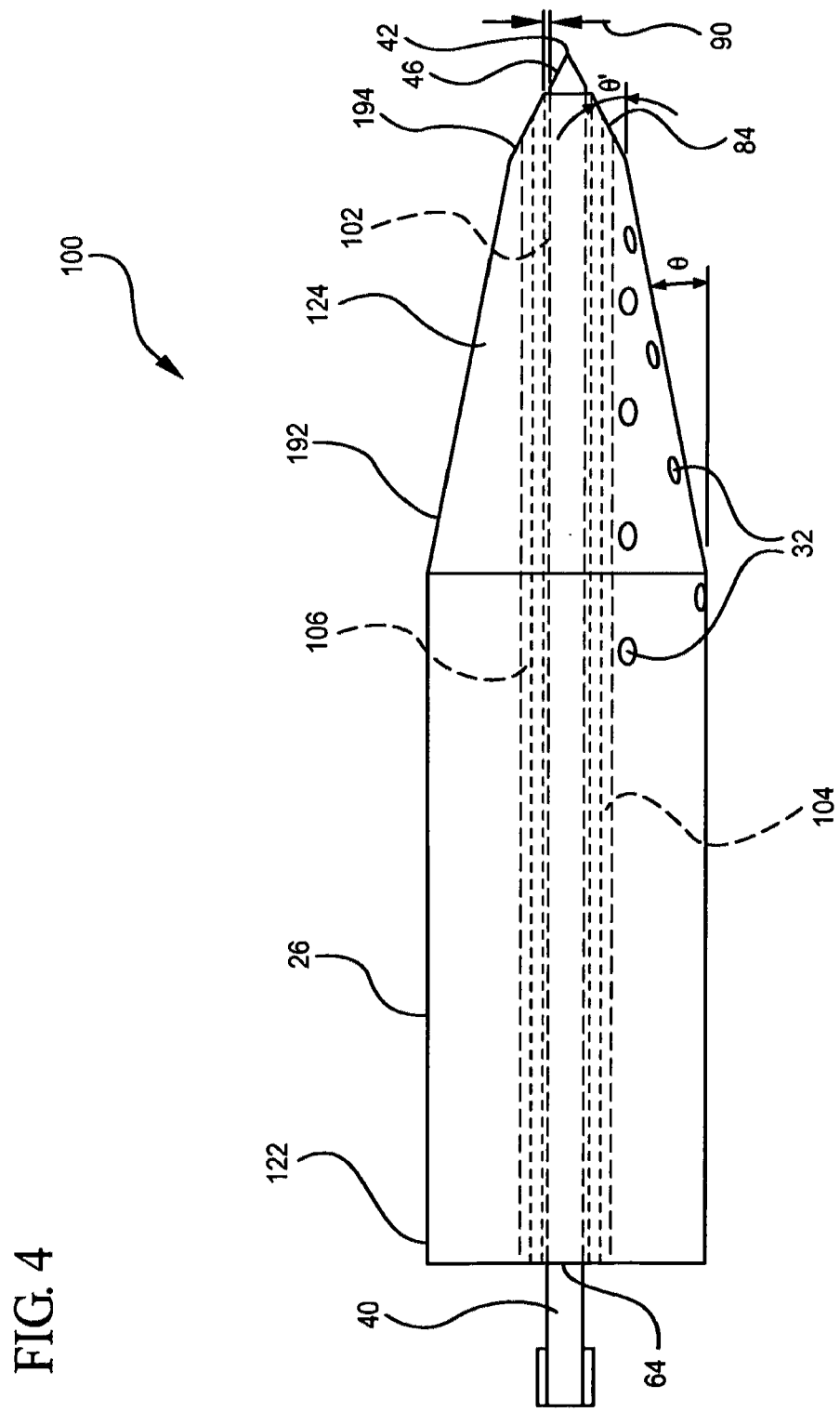
FIG. 4 is a perspective view of an implementation of a multi-lumen primable catheter incorporating a supportive trocar.
Figure 5:
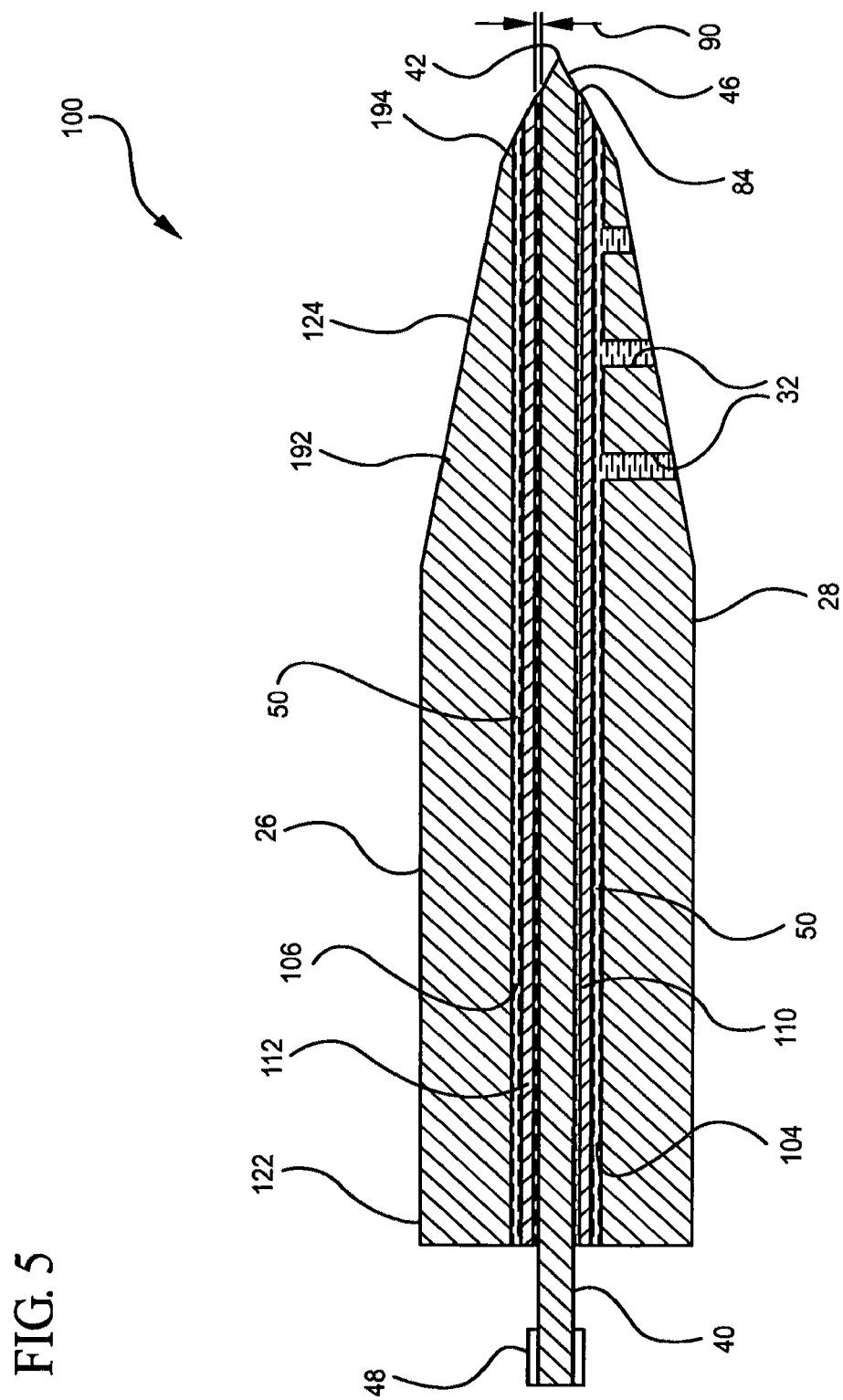
FIG. 5 is a cross-sectioned view of an implementation of a multi-lumen primable catheter incorporating a supportive trocar.
Figure 6A:
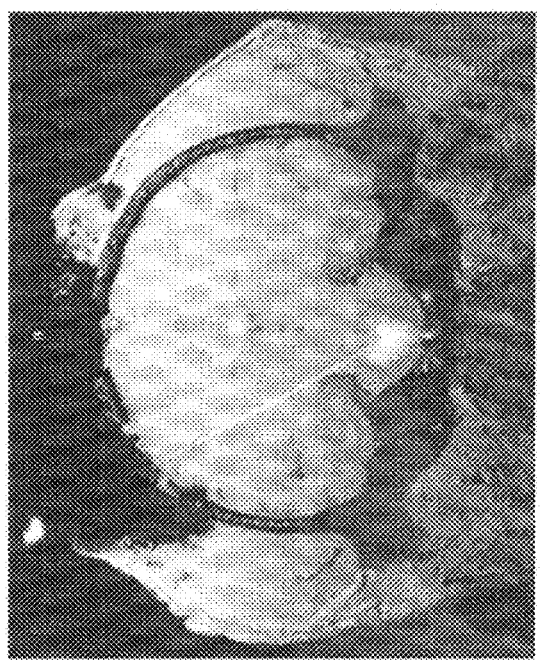
FIGS. 6A through 6D are MRI images of a CED procedure utilizing a primable intracranial catheter delivery system in accordance with a representative embodiment of the present invention.
Figure 6B:
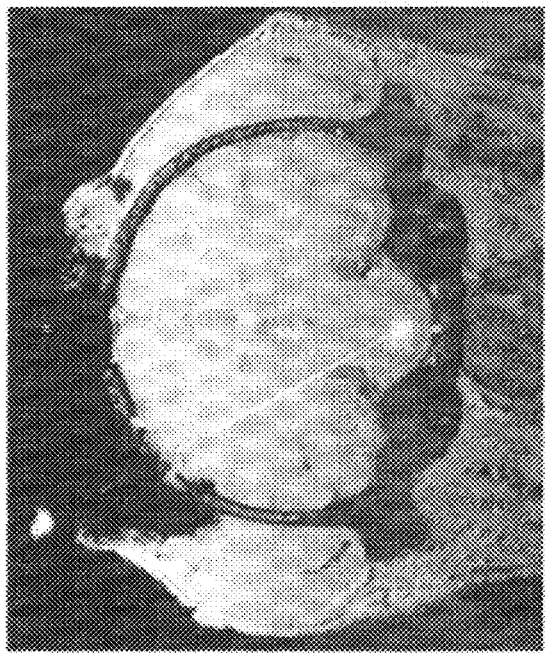
Figure 6D:
Figure 6C:
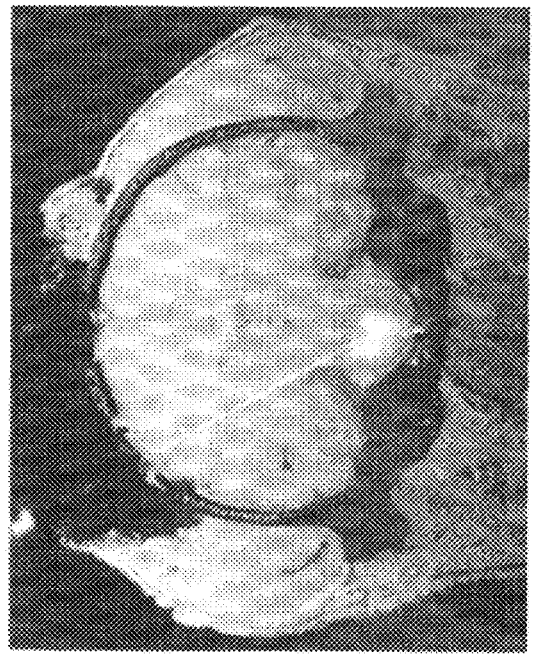

The trocar 40 generally includes a wire having a sharpened end 42 and a shaft 44. The trocar 40 is inserted through the lumen of the catheter 20 so that a pointed blunt end 42 of the trocar 40 extends beyond the tip end 24 of the catheter. Additionally, the trocar 40 is positioned within the lumen of the catheter 20 so that a portion of the shaft 44 extends beyond the base end 22 of the catheter 20. The sharpened end 42 of the trocar 40 generally includes a chamfered cutting edge 46 that is configured to provide an opening in a target tissue through which the catheter 20 is inserted. In some embodiments, the trocar 40 comprises a relatively rigid material, such as an MRI compatible metal. Examples of non-ferrous MRI compatible metals include, but are not limited to, titanium and shaped memory alloy (SMA) materials such as Nitinol or Flexinol®. The gauge of the trocar 40 is selected such that the outer diameter of the trocar 40 is smaller than the inner diameter of the catheter 20, as shown in FIGS. 2, 4, and 5, below. In addition to providing an opening in the target tissue, the trocar 40 provides rigidity and control to the otherwise insufficient rigidity of the polymer catheter material.

In some embodiments, a portion of the shaft 44 is configured to compatibly receive or couple to a micromanipulator (not shown) to control the placement of the catheter in a target tissue. For example, in some embodiments a base portion 22 of the shaft 44 includes outwardly extended flanges 48 to provide a coupling surface for the micromanipulator. In other embodiments, the micromanipulator is further connected to a computer having a software program designed to control the micromanipulator in accurately and carefully guiding the catheter 20 into a desired position. In other embodiments, the base end 22 of the catheter 20 is further modified to couple to a fluid injection source, such as a syringe or a pump (not shown). In other embodiments, the fluid injection source further includes means for controlling the flow rate of the fluid through the catheter 20, such as via a clamp or a speed control attached to a pump.

Following placement of the catheter 20, the trocar 40 is removed from the inner lumen 30 of the catheter 20, and the lumen 30 is then used to infuse a therapeutic to a target region of the tissue. In some embodiments of the present invention, the catheter 20 further includes a plurality of side-ports 32. The side-ports 32 comprise a plurality of ports or holes providing a pathway between the inner lumen 30 and the outer surface 28 of the catheter 20. The side-ports 32 provide multiple exit points for the infused therapeutic, thereby providing a diffusing effect to the target tissue. In some embodiments, the plurality of side-ports 32 is positioned on the tip end 24 of the catheter 20. In other embodiments, the plurality of side-ports 32 is positioned both on the tip end 24 and the middle portion 26 of the catheter 20. Still, in other embodiments the position of the plurality of side-ports 32 is limited to the middle portion 26 of the catheter 20.

Referring now to FIG. 2, a cross-sectioned view of a primable catheter system 10 is shown. A portion of the inner lumen 30 of the catheter 20 comprises a fluid reservoir 60 having first inner diameter 70. A distal end 62 of the fluid reservoir 60 comprises an opening 64 through which a priming fluid 50 is injected into and throughout the inner lumen 30 of the catheter 20. A proximal end 66 of the fluid reservoir comprises a chamfered narrowing 80 that reduces the first inner diameter 70 to a second diameter 72. The second diameter 72 corresponds to a nozzle portion 82 of the catheter 20. The proximal end 66 further includes an aperture 84 through which a fluid exits the catheter 20. In some embodiments, the sharpened end 42 of the trocar 40 is positioned in the aperture 84 such that the cutting edge 46 is positioned external to the inner lumen 30.

In some implementations of the present invention, the outer diameter 48 of the trocar 40 is less than the second inner diameter 72 of the catheter 20. As such, a gap 90 is provided between the outer surface 52 of the trocar and the inner surface 34 of the inner lumen 30. The gap 90 provides an unobstructed pathway through the lumen 30 whereby a priming fluid 50 is injected throughout the inner lumen 30 to displace trapped air within the catheter 20. The gap 90 further permits priming of the side-ports 32 to purge air therein. Priming fluids may include any solution that is compatible with the intended therapeutic as well as the targeted tissue. For example, in some embodiments the priming fluid is a saline solution.

The outer surface 28 of the catheter 20 may further include a coating 36 to aid in the placement of the catheter 20. For example, in some embodiments the outer surface 28 of the catheter 20 is treated with active agents to prevent platelet formation and blood clotting. In some embodiments the outer surface 28 is coated with an anticoagulant coating 36. In other embodiments, the outer surface 28 of the catheter 20 is coated with a lubricant 36 such as a water-based, water-soluble lubricant. Additional coating materials, such as a radiopaque coating material 36 are further beneficial to provide visualization of the tip end 24 during placement of the catheter 20.

Figure 3:
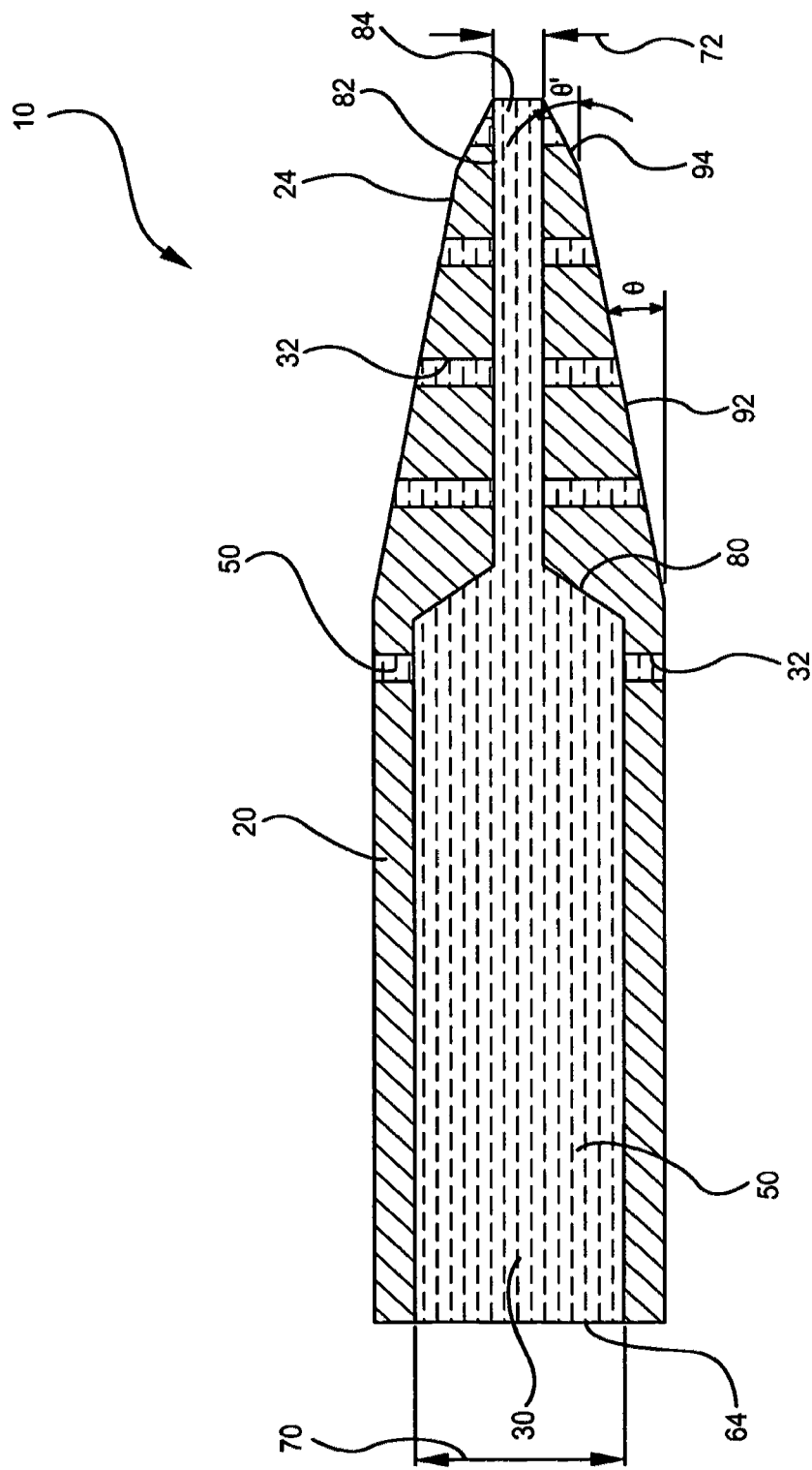
FIG. 3 is a cross-sectioned view of an implementation of a primable catheter system following removal of a supportive trocar.

The tip end 24 of the catheter 20 is configured to provide a consistent, smooth transition from catheter 20 to trocar 40. The smooth transition provides for less tissue trauma and greater patient comfort. The unique tip design includes a multi-chamfered outer surface 28 to provide a gradual transition from the outer surface 28 of the middle portion 26 to the diameter 72 of the aperture 84. Referring now to FIG. 3, a cross-sectioned view of a primable catheter system 10 is shown following removal of the trocar 40. The tip end 24 of the catheter 20 includes a first chamfered surface 92 and a second chamfered surface 94. The first chamfered surface 92 is positioned directly adjacent to the middle portion 26 of the catheter 20 and includes a chamfer angle θ selected from about 1° to about 30°. In some embodiments, the first chamfered surface 92 comprises a chamfer angel θ selected from about 10° to about 20°. In other embodiments, the first chamfered surface 92 comprises a chamfer angle θ of about 15°.

The tip end 24 further includes a second chamfered surface 94 positioned between the first chamfered surface 92 and the aperture 84 opening. The second chamfered surface 94 includes a chamfer angle θ' selected from about 25° to about 45°. In some embodiments, the second chamfered surface 94 comprises a chamfer angle θ' selected from about 30° to about 40°. In other embodiments, the second chamfered surface 94 comprises a chamfer angle θ' of about 35°. The chamfer angles θ and θ' of the first and second chamfered surfaces 92 and 94 progressively increase such that the tip end 24 of the catheter 20 tapers inwardly from the middle portion 26 to the aperture 84. Thus, the chamfer angle θ of the first chamfered surface 92 is always less than, or equal to the chamfer angle θ' of the second chamfered surface 94.

Referring now to FIG. 4, a perspective view of a multi-lumen primable catheter 100 is shown. In some implementations of the present invention, the catheter 100 may include a primary or first lumen 102, a secondary or second lumen 104, and a tertiary or third lumen 106. In some embodiments, the catheter 100 includes a first lumen 102 and a second lumen 104. In other embodiments, the catheter 100 includes a first lumen 102, a second lumen 104 and a third lumen 106. Each lumen 102, 104 and 106 includes a base end 122 and a tip end 124, wherein the lumen 102, 104, and 106 provide fluid communication between the base end 122 and the tip end 124 of the catheter 100. In some embodiments, the first lumen 102 is configured to compatibly house a trocar 40 in a manner similar to the above described embodiments. In other embodiments, the tip end 124 further includes a first chamfered surface 192 and a second chamfered surface 194, having respective chamfer angles θ and θ' as previously discussed. Further, in some embodiments a portion of the catheter 100 includes a plurality of side-ports 32 to diffuse an injected therapeutic.

In some embodiments, a first lumen 102 is required to house a trocar 40, while a second lumen 104 is required to deliver a therapeutic or other fluid to a target tissue. In other embodiments, the gap 90 between the trocar 40 and the aperture 84 is eliminated, thereby requiring that a fluid be injected through a second lumen 104. As such, the second lumen 104 is pre-primed with a priming fluid to displace air within the lumen 104. In other embodiments, a third lumen 106 is provided to monitor and control fluid flow through the catheter 100. For example, in some embodiments a sensor is inserted into the third lumen 106 and positioned proximate to the fluid flow so as to obtain and relay infusion data to external monitoring equipment.

Referring now to FIG. 5, a cross-sectioned view of the multi-lumen catheter 100 is shown. In some embodiments, the first lumen 102 is separated from the second lumen 104 via a first membrane wall 110. In other embodiments, the first lumen 102 is separated from the third lumen 106 via a second membrane wall 112. Those of skill in the art will appreciate that a multi-lumen catheter 100 may be manufactured using any variety of plastic molding, injection and joining methods common to the art. In other embodiments, the catheter 100 comprises a metallic material and therefore does not require the use of a trocar 40. Still in other embodiments, the middle portion 26 of the catheter 100 is modified to include a set of threads or other coupling means for attaching the catheter 100 to an external device (not shown) thereby securing the position of the catheter on a patient or other surface. The base end 122 of the catheter 100 may also include an adapter or other means for providing fluid flow through the catheter 100 for priming or infusing a fluid through the catheter 100.

In some implementations of the present invention, the primable catheters 10 and 100 are pre-primed prior to insertion into a target tissue. For example, in some embodiments the base ends 22 and 122 of the catheter 10 and 100 are attached to a fluid source (not shown) and subsequently injected with a priming fluid 50 to purge or displace air present within the catheters 10 and 100. The priming step completely removes air from the catheter 10 and 100 and fills the lumens 30, 102, 104 and 106 with the priming fluid. Following the priming step, the catheter 10 or 100 is inserted into a target tissue. In some embodiments, a radiograph is used to aid in placement of the catheter 10 or 100. In other embodiments, a computer operated micromanipulator is used to aid in placement of the catheter 10 or 100. Following placement of the catheter 10 or 100, the trocar 40 is removed from the respective lumen 30 or 102 and the lumen 30 or 102 is then accessed to infuse a therapeutic or other fluid to the target tissue. In some embodiments, the trocar 40 remains in the lumen 102 and ancillary lumens 104 and 106 are used to infuse the desired therapeutic to the target tissue.

EXAMPLES

Referring now to FIGS. 6A through 6D, an intracranial catheter delivery system in accordance with the present invention was implanted into the pons of a non-human primate model. An access hole was first provided through the skull of the patient at a location proximal to the treatment site so as to facilitate placement of the Vialon catheter via a Nitinol trocar. Prior to insertion, air within the catheter was purged with a priming solution. Once the catheter was placed within the patient's brain, targeted, localized delivery of an imaging agent was accomplished.

FIGS. 6A through 6D show four sequential MRI images taken during the infusion procedure. These images illustrate the progressive infusion of the imaging agent into the pons of the brain. Over the course of the procedure, an increasingly larger spot was formed and maintained at the end of the catheter without any signs of retrograde or leak back flow along the catheter. Furthermore, post operative examination of the patient revealed minimal damage or trauma to the targeted tissue of the patient.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A primable catheter assembly for use in targeted drug delivery applications, the assembly comprising:
   a catheter having a lumen, a base end, a tip end, an inner diameter, and an outer diameter, a portion of the outer diameter having a first chamfered surface corresponding to the tip end of the catheter, and the inner diameter having a narrowed portion also corresponding to the tip end of the catheter; and
   a trocar slidably positioned within the catheter and including a shaft having a first end, a second end, and an outer diameter, the trocar further including a tip that extends from the first end of the shaft, the shaft having a length that causes the tip to extend beyond the tip end of the catheter and the second end to extend beyond the base end of the catheter, the outer diameter of the shaft being smaller than the narrowed portion of the inner diameter of the catheter such that a primable gap exists between an outer surface of the shaft and an inner surface of the catheter while the tip of the trocar extends beyond the tip end of the catheter;
   the catheter including an interface for coupling a fluid source to the catheter while the trocar is positioned within the catheter, the interface being in fluid communication with the primable gap such that priming fluid provided by the fluid source flows through the primable gap and out through the tip end of the catheter when the trocar is positioned within the catheter with the tip of the trocar extending beyond the tip end of the catheter.

2. The assembly of claim 1, wherein the first chamfered surface further includes a second chamfered surface, the first chamfered surface having a chamfer angle from about 1° to about 30°, and the second chamfered surface having a chamfer angle from about 25° to about 45°.

3. The assembly of claim 2, wherein the chamfer angle of the second chamfered surface is greater than the chamfer angle of the first chamfered surface.

4. The assembly of claim 1, wherein the priming fluid prevents entrapment of air between the outer surface of the trocar and the inner surface of the catheter.

5. The assembly of claim 1, wherein the tip end of the catheter further comprises a plurality of ports providing pathways between an outer surface of the catheter and the inner surface of the catheter.

6. The assembly of claim 1, wherein the catheter comprises a thermoreactive, viscoelastic polymer.

7. The assembly of claim 6, wherein the catheter further comprises a radiopaque coating.

8. The assembly of claim 1, wherein the catheter is metallic.

9. The assembly of claim 1, wherein an outer surface of the catheter is coated with an anticoagulant.

10. The assembly of claim 1, further comprising an interface surface forming a portion of the base end of the catheter, and configured to receive a micromanipulator.

11. The assembly of claim 1, wherein a portion of the primable gap tapers inwardly towards the trocar.

12. The assembly of claim 1, further comprising a second lumen running parallel to the lumen of the catheter, wherein the lumen houses the trocar, and the second lumen provides a pathway through which a therapeutic is delivered to a targeted region of a tissue.

13. The assembly of claim 12, further comprising a third lumen running parallel to the lumen and the second lumen of the catheter, wherein the third lumen provides monitoring and flow control of the therapeutic being delivered.

14. The assembly of claim 1, wherein the trocar is visible by imaging.

15. The assembly of claim 1, wherein the catheter comprises a non-ferrous MRI compatible metal.

16. A method for manufacturing a primable catheter assembly for use in targeted drug delivery applications, the method comprising:
   providing a catheter having a lumen, a base end, a tip end, an inner diameter, and an outer diameter;
   chamfering an outer surface of the catheter to provide a first chamfered surface corresponding to the tip end of the catheter;
   positioning a trocar within the lumen of the catheter, the trocar having a shaft having a first end, a second end, and an outer diameter, the trocar further including a tip that extends from the first end of the shaft, the shaft having a length that causes the tip to extend beyond the tip end of the catheter and the second end to extend beyond the base end of the catheter, the outer diameter of the shaft being smaller than the inner diameter of the catheter such that a primable gap exists between an outer surface of the shaft and an inner surface of the catheter while the tip of the trocar extends beyond the tip end of the catheter; and
   providing an interface for coupling a fluid source to the catheter while the trocar is positioned within the catheter, the interface being in fluid communication with the primable gap such that priming fluid provided by the fluid source flows through the primable gap and out through the tip end of the catheter when the trocar is positioned within the catheter with the tip of the trocar extending beyond the tip end of the catheter.

17. The method of claim 16, further comprising chamfering the outer surface of the catheter to provide a second chamfered surface, the first chamfered surface having a chamfer angle from about 1° to about 30°, and the second chamfered surface having a chamfer angle from about 25° to about 45°, wherein the chamfer angle of the second chamfered surface is greater than the chamfer angle of the first chamfered surface.

18. The method of claim 16, further comprising priming the primable gap with a priming fluid, wherein the priming fluid expels air present within the primable gap.

19. The method of claim 16, further comprising adapting the base end of the catheter to receive a micromanipulator.

20. The method of claim 16, further comprising coating a portion of the catheter with at least one of an anticoagulant and a radiopaque material.

21. A catheter assembly comprising:
a catheter having an inner surface forming a lumen, the inner surface having a first diameter at a base end of the catheter and a second diameter at a tip end of the catheter, the second diameter being less than the first diameter; and a trocar positioned within the lumen of the catheter and extending out through an opening at the tip end of the catheter, a shaft of the trocar having a diameter that is less than the second diameter such that a gap exists between the inner surface of the catheter and the shaft of the trocar when the trocar is positioned within the lumen with a tip of the trocar positioned beyond the tip end of the catheter;

the catheter including an interface for coupling a fluid source to the catheter while the trocar is positioned within the catheter, the interface being in fluid communication with the gap such that priming fluid provided by the fluid source flows through the gap and out through the tip end of the catheter when the trocar is positioned within the catheter with the tip of the trocar positioned beyond the tip end of the catheter.

* * * * *